(12) United States Patent
Arndt et al.

(10) Patent No.: US 12,097,205 B2
(45) Date of Patent: *Sep. 24, 2024

(54) AQUEOUS COMPOSITION, IN PARTICULAR FOR TREATING MUCOSA AND/OR WOUNDS

(71) Applicant: B. Braun Melsungen AG, Melsungen (DE)

(72) Inventors: Andreas Arndt, Kriens (CH); Natalie Dück, Nottwil (CH); Michael Kurz, Oberkirch (CH)

(73) Assignee: B. Braun Melsungen AG, Melsungen (DE)

( * ) Notice: Subject to any disclaimer, the term of this patent is extended or adjusted under 35 U.S.C. 154(b) by 740 days.

This patent is subject to a terminal disclaimer.

(21) Appl. No.: 17/293,100

(22) PCT Filed: Oct. 23, 2019

(86) PCT No.: PCT/EP2019/078868
§ 371 (c)(1),
(2) Date: May 12, 2021

(87) PCT Pub. No.: WO2020/108880
PCT Pub. Date: Jun. 4, 2020

(65) Prior Publication Data
US 2021/0401848 A1 Dec. 30, 2021

(30) Foreign Application Priority Data
Nov. 29, 2018 (DE) .................... 10 2018 220 624.4

(51) Int. Cl.
| A61K 31/53 | (2006.01) |
| A61K 9/08 | (2006.01) |
| A61K 47/10 | (2017.01) |
| A61K 47/18 | (2017.01) |
| A61K 47/26 | (2006.01) |
| A61K 47/32 | (2006.01) |
| A61K 47/34 | (2017.01) |

(52) U.S. Cl.
CPC .............. *A61K 31/53* (2013.01); *A61K 9/08* (2013.01); *A61K 47/10* (2013.01); *A61K 47/18* (2013.01); *A61K 47/186* (2013.01); *A61K 47/26* (2013.01); *A61K 47/32* (2013.01); *A61K 47/34* (2013.01)

(58) Field of Classification Search
CPC ........... A61K 31/53; A61K 47/34; A61K 9/08
See application file for complete search history.

(56) References Cited

U.S. PATENT DOCUMENTS

| 6,686,358 B2 | 2/2004 | De Nanteuil et al. |
| 7,388,020 B2 | 6/2008 | Eriksson et al. |
| 8,236,357 B2 | 8/2012 | Bobbert |
| 2005/0119313 A1 | 6/2005 | Behrends et al. |
| 2009/0041813 A1 | 2/2009 | Bouillo et al. |
| 2009/0255064 A1 | 10/2009 | Jungen et al. |
| 2022/0265665 A1 | 8/2022 | Le Meur et al. |

FOREIGN PATENT DOCUMENTS

| AR | 035230 A1 | 5/2004 |
| CN | 1358723 A | 7/2002 |
| CN | 106474053 A | 3/2017 |
| DE | 10205883 A1 | 8/2003 |
| EP | 0411315 A1 | 2/1991 |
| EP | 1574503 A1 | 9/2005 |
| JP | S62289529 A | 12/1987 |
| JP | 2009511757 A | 3/2009 |
| JP | 2010513244 A | 4/2010 |

(Continued)

OTHER PUBLICATIONS

"Foaming, foam films, antifoaming and defoaming" by Pugh, Adv. Colloid Interface Sci. 64, 67-142 (Year: 1996).*

(Continued)

*Primary Examiner* — Theodore R. Howell
(74) *Attorney, Agent, or Firm* — Christopher A. Rothe; Culhane PLLC

(57) ABSTRACT

An aqueous composition includes a dihydrotriazine compound of the general formula below,

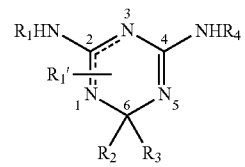

where $R_1$ means (i) a phenyl group or phenylalkyl group, (ii) a naphthyl group or naphthylalkyl group, (iii) a heterocyclic group, heterocyclic alkyl group or heterocyclic aminoalkyl group, (iv) an alkyl group having 1 to 16 carbon atoms or (v) a cycloalkyl group or cycloalkylalkyl group, $R_1'$ means a hydrogen atom bonded to the nitrogen atom at position 1 or 3 of the dihydrotriazine ring, $R_2$ and $R_3$ each mean a hydrogen atom or a methyl group, $R_4$ means an alkyl group having 7 to 16 carbon atoms and the dashed line indicates that a double bond is positioned either between positions 1 and 2 or between positions 2 and 3 of the dihydrotriazine ring, or a tautomer thereof or a salt thereof and a defoamer.

24 Claims, No Drawings

(56) References Cited

FOREIGN PATENT DOCUMENTS

| JP | 2016505558 | A  | 2/2016  |
|----|------------|----|---------|
| RU | 2437928    | C2 | 12/2011 |
| RU | 2535016    | C2 | 12/2014 |
| RU | 2653488    | C2 | 5/2018  |
| WO | 03004013   | A1 | 1/2003  |
| WO | 2007031520 | A2 | 3/2007  |
| WO | 2015107183 | A1 | 7/2015  |

OTHER PUBLICATIONS

Schülke & Mayr Gmbh, Inter Alia the German Federal Institute for Drugs and Medical Devices, https://www.bfarm.de/SharedDocs/Risikoinformationen/Pharmakovigilanz/DE/RHB/2011/rhb-octenisept.html, Jan. 21, 2011, 2 pages, with translation.

Thompson, et al., "Studies on a Dihydrotriazine and a Sulfone, Alone and in Combination, Against Plasmodium Berghei in Mice," American Journal of Tropical Medicine & Hygiene, American Society of Tropical Medicine and Hygiene, Mar. 1, 1965, 6 pages.

Schülke & Mayr Gmbh, inter alia, The German Federal Institute for Drugs and Medical Devices, https://www.bfarm.de/SharedDocs/Risikoinformationen/Pharmakovigilanz/DE/RHB/2011/rhb-octenisept.html, Jan. 21, 2011, 2 pages.

Written Opinion received in International Application No. PCT/EP2019/078868, dated Jan. 17, 2020, with translation, 12 pages.

International Search Report received in International Application No. PCT/EP2019/078868, dated Jan. 17, 2020, with translation, 4 pages.

Office Action received in Japanese Application No. 2021-531014 dated Oct. 5, 2023, with partial translation, 3 pages.

Okunishi et al., "In vitro evaluation of the antimicrobial activity of HM-242, a novel antiseptic compound," The Journal of Antibiotics (2009), Jul. 3, 2009, 5 pages.

Office Action received in Chinese Application No. 201980078937.1 dated Nov. 27, 2023, with translation, 20 pages.

Zhou et al., "Study on pseudo-ternary phase diagrams and properties of microemulsion injection," Chin Med Biotechnol, Apr. 2008, vol. 3, No. 2, with translation, 5 pages.

Office Action received in Russian Application No. 2021118366/04 dated Apr. 26, 2023, with translation, 9 pages.

Search Report received in Russian Application No. 2021118366/04 dated Apr. 25, 2023, with translation, 5 pages.

\* cited by examiner

AQUEOUS COMPOSITION, IN PARTICULAR FOR TREATING MUCOSA AND/OR WOUNDS

CROSS-REFERENCE TO RELATED APPLICATIONS

This application is the United States national phase entry of International Application No. PCT/EP2019/078868, filed Oct. 23, 2019, and claims the benefit of priority of German Application No. 10 2018 220 624.4, filed Nov. 29, 2018. The contents of International Application No. PCT/EP2019/078868 and German Application No. 10 2018 220 624.4 are incorporated by reference herein in their entireties.

FIELD

The invention relates to an aqueous composition which is especially suitable for treating mucosa and/or wounds.

BACKGROUND

Iodine-containing products which contain the iodine in the form of iodophors, for example povidone-iodine, have become established for the treatment of mucosa and wounds. They are distinguished by good tolerability. The use of these agents is limited because of possible allergies and sensitizations, but also because of the known absorption of iodine by the organism.

It is for this reason that products containing cationic antimicrobial agents have been proposed.

An aqueous, polyhexamethylene biguanide-containing composition which can be especially in the form of a wound irrigation solution or a wound gel is known from WO 03/004013 A1.

The subject matter of DE 102 05 883 A1 is an aqueous antiseptic based on bispyridinium alkanes.

WO 2007/031520 A2 relates to the use of octenidine dihydrochloride for production of a pharmaceutical composition for, inter alia, treatment of wounds.

Conventional agents have the disadvantage that they are ineffective against fungi, especially yeasts.

An octenidine-containing preparation available under the registered trademark OCTENISEPT® can show good mucosal compatibility, but it can lead to intolerances right up to necroses when used in deeper wounds. This has been published by, inter alia, the German Federal Institute for Drugs and Medical Devices: www.bfarm.de(/).

An octenidine-containing composition is known from EP 0 411 315 A1.

SUMMARY

It is an object of the invention to provide a very highly tolerated composition which is suitable for treating mucosa and/or wounds and has, at the same time, an improved efficacy against fungi, especially yeasts.

The composition according to the invention is an aqueous, i.e., water-containing, composition. The aqueous composition is preferably in the form of an aqueous solution, i.e., in the form of a water-containing solution, or in the form of a hydrogel, i.e., in the form of a water-containing gel.

The aqueous composition comprises the following:
a dihydrotriazine compound of the general formula I below:

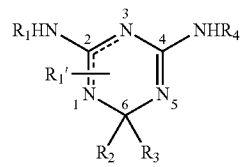

Formula I wherein
$R_1$ means (i) a phenyl group or a phenylalkyl group, each of which is optionally substituted with 1 to 3 substituents selected from the group consisting of $C_{1-6}$-alkoxy group, hydroxy group, a halogen atom, $C_{1-6}$-haloalkyl group, $C_{1-6}$-alkyl group, a sulfonamido group and $C_{1-6}$-haloalkoxy group, (ii) a naphthyl group or a naphthylalkyl group, (iii) a heterocyclic group, a heterocyclic alkyl group or a heterocyclic aminoalkyl group, (iv) an alkyl group having 1 to 16 carbon atoms or (v) a cycloalkyl group or a cycloalkylalkyl group, $R_1'$ means a hydrogen atom which is bonded to the nitrogen atom at position 1 or 3 of the dihydrotriazine ring, $R_2$ and $R_3$ independently of one another mean a hydrogen atom or a methyl group, $R_4$ means an alkyl group having 7 to 16 carbon atoms and the dashed line indicates that the position of a double bond is either between positions 1 and 2 or between positions 2 and 3 of the dihydrotriazine ring, or a tautomer thereof, i.e., a tautomer of the dihydrotriazine compound of the general formula I, or a salt, especially a pharmacologically acceptable salt, thereof, i.e., a salt, especially a pharmacologically acceptable salt, of the dihydrotriazine compound of the general formula I, and a defoamer.

The aqueous composition is especially suitable for prevention, i.e., prophylaxis, or treatment of mucosa and/or wounds, preferably acute or chronic wounds, and/or for prevention, i.e., prophylaxis, or treatment of infections and/or for prevention, i.e., prophylaxis, or treatment of infectious diseases, such as, for example, erysipelas. In the context of the present invention, the aqueous composition can therefore also be referred to as an aqueous wound-treatment composition, especially an aqueous antiseptic composition. The aqueous composition is preferably an aqueous wound irrigation solution.

In the context of the present invention, the expression "dihydrotriazine compound" is to be understood to mean a compound having a six-membered triazine ring having only two double bonds, i.e., a so-called dihydrotriazine ring, wherein the triazine ring or dihydrotriazine ring has a ring nitrogen atom at each of positions 1, 3 and 5 and a ring carbon atom at each of positions 2, 4 and 6 and wherein the position of one of the double bonds is between positions 4 and 5 of the triazine ring or dihydrotriazine ring and the position of the other double bond, i.e., second or remaining double bond, is either between positions 1 and 2 or between positions 2 and 3 of the triazine ring or dihydrotriazine ring.

In the context of the present invention, the expression "defoamer" is to be understood to mean a compound which is capable of slowing down weakening, i.e., diminishing or reducing, or avoiding foaming.

In the context of the present invention, the expression "surfactant" is to be understood to mean a compound which lowers the surface tension of a liquid, especially of water or an aqueous liquid, and/or the interfacial tension between two phases and allows or assists the formation of dispersions and/or acts as a solubilizer.

In the context of the present invention, the expression "emulsifier" is to be understood to mean a compound which is capable of mixing two immiscible liquids, such as, for example, oil and water, to form an emulsion and of, in particular, stabilizing them.

In the context of the present invention, the expression "fungi" can mean unicellular or multicellular fungi.

In the context of the present invention, the expression "yeasts" is to be understood to mean unicellular fungi which multiply by budding or division (splitting) (so-called yeast fungi).

In the context of the present invention, the expression "phenyl group" is to be understood to mean a benzene radical, i.e., the atom group —$C_6H_5$.

In the context of the present invention, the expression "benzyl group" is to be understood to mean the phenylmethyl group —$CH_2$-$C_6H_5$, previously also referred to as α-tolyl group.

In the context of the present invention, the expression "phenylalkyl group" means a group in which a linear, i.e., unbranched, or branched alkyl group or alkylene group, especially having 1 to 6 carbon atoms, is bonded to a phenyl group. The alkyl group or alkylene group can be a substituted or unsubstituted alkyl group or alkylene group. The phenylalkyl group is preferably a benzyl group, methylbenzyl group such as, in particular, 4-methylbenzyl group, 1-phenylethyl group, 2-phenylethyl group, 1-phenylpropyl group, 2-phenylpropyl group or 3-phenylpropyl group.

A benzene ring of the phenyl group or phenylalkyl group can have one to three substituents, especially selected from the group consisting of halogen atom, hydroxy group, $C_{1-6}$-alkyl group, $C_{1-6}$-haloalkyl group, $C_{1-6}$-alkoxy group, $C_{1-6}$-haloalkoxy group and sulfonamido group.

In the context of the present invention, the expression "halogen atom" can mean a fluorine atom, a chlorine atom, a bromine atom or an iodine atom.

In the context of the present invention, the expression "$C_{1-6}$-alkyl group" can mean a relevant alkyl group, i.e., an alkyl group having 1 to 6 carbon atoms, that is linear or branched. The alkyl group can be a substituted or unsubstituted alkyl group. For example, the $C_{1-6}$-alkyl group can be a methyl group, ethyl group, n-propyl group, isopropyl group, n-butyl group, isobutyl group, sec-butyl group, tert-butyl group, n-pentyl group, sec-pentyl group, isopentyl group, neopentyl group, n-hexyl group or isohexyl group.

In the context of the present invention, the expression "$C_{1-6}$-haloalkyl group" can especially mean a chloromethyl group, bromomethyl group, 1-chloroethyl group or trifluoromethyl group.

In the context of the present invention, the expression "$C_{1-6}$-alkoxy group" can especially mean a methoxy group, ethoxy group, n-propoxy group, isopropoxy group, n-butoxy group or isobutoxy group.

In the context of the present invention, the expression "$C_{1-6}$-haloalkoxy group" can especially mean a trifluoromethoxy group.

In the context of the present invention, the expression "naphthyl group" can mean a 1-naphthyl group or a 2-naphthyl group.

In the context of the present invention, the expression "naphthylalkyl group" means a group in which a linear, i.e., unbranched, or branched alkyl group, especially having 1 to 6 carbon atoms, is bonded to a naphthyl group. The alkyl group can be a substituted or unsubstituted alkyl group. The naphthylalkyl group is preferably a 1-naphthylmethyl group, 2-naphthylmethyl group, 1-naphthylethyl group or 2-naphthylethyl group.

In the context of the present invention, the expression "heterocyclic group" means a three- to six-membered heterocyclic group which contains one to three atoms selected from the group consisting of nitrogen atom, oxygen atom and sulfur atom, it being possible for a benzene ring to be fused to the heterocyclic group. The heterocyclic group can be, for example, a pyridyl group, a pyrazinyl group, a thiazolyl group, a piperidyl group, a piperazyl group, a tetrahydrofuryl group, a thienyl group, a pyrrolyl group, a pyrrolidinyl group, an oxazolyl group, an imidazolyl group, an isooxazolyl group, an isothiazolyl group, a pyrazolyl group, a tetrahydropyranyl group, a 2-oxotetrahydropyranyl group, a pyrimidinyl group, a pyradizinyl group, a morpholinyl group, a 1,3,5-triazinyl group, a 1,2,4-triazinyl group, a quinolyl group or an isoquinolyl group.

In particular, the heterocyclic group in the context of the present invention can be a 2-pyridyl group, a 3-pyridyl group, a 4-pyridyl group, a 2-furyl group, a 2-thiazolyl group, a 1-piperidyl group, a 1-piperazyl group, a 2-quinolyl group, a 3-quinolyl group, a 4-quinolyl group, a 5-quinolyl group, an 8-quinolyl group, a 1-isoquinolyl group, a 3-isoquinolyl group, a 4-isoquinolyl group or a 5-isoquinolyl group.

In the context of the present invention, the expression "heterocyclic alkyl group" means a group in which a linear, i.e., unbranched, or branched alkyl group, especially having 1 to 6 carbon atoms, is bonded to a heterocyclic group, especially as defined or described in the preceding paragraphs. The alkyl group can be a substituted or unsubstituted alkyl group. The heterocyclic alkyl group is preferably a 2-pyridylmethyl group, 3-pyridylmethyl group, 4-pyridylmethyl group, 2-pyridylethyl group, 3-pyridylethyl group, 4-pyridylethyl group, pyrazinylmethyl group, pyrazinylethyl group, 2-furylmethyl group, 2-furylethyl group, 2-thiazolylmethyl group, 2-thiazolylethyl group, 4-piperidylmethyl group, 2-quinolylmethyl group, 3-quinolylmethyl group, 4-quinolylmethyl group, 5-quinolylmethyl group, 8-quinolylmethyl group, 1-i soquinolylmethyl group, 3-isoquinolylmethyl group, 4-isoquinolylmethyl group or 5-isoquinolylmethyl group.

In the context of the present invention, the expression "heterocyclic aminoalkyl group" means a group in which a linear, i.e., unbranched, or branched alkyl group, especially having 1 to 12 carbon atoms, is bonded to a heterocyclic amino group. The alkyl group can be a substituted or unsubstituted alkyl group. The heterocyclic aminoalkyl group is preferably a 4-amino-dihydro-1,3,5-triazin-2-yl-amino group, a 4-alkylamino-dihydro-1,3,5-triazin-2-yl-amino group or 4-phenylalkylamino-dihydro-1,3,5-triazin-2-yl-amino group.

In the context of the present invention, the expression "alkyl group having 1 to 16 carbon atoms" means a linear, i.e., unbranched, or branched alkyl group having 1 to 16 carbon atoms. The alkyl group can be a substituted or unsubstituted alkyl group. The alkyl group having 1 to 16 carbon atoms is preferably a methyl group, ethyl group, n-propyl group, isopropyl group, n-butyl group, isobutyl group, sec-butyl group, tert-butyl group, n-hexyl group, n-heptyl group, n-octyl group, tert-octyl group, n-nonyl group, n-decyl group, n-undecyl group, n-dodecyl group, n-tridecyl group, n-tetradecyl group, n-pentadecyl group or n-hexadecyl group.

In the context of the present invention, the expression "cycloalkyl group" especially means a cycloalkyl group having 3 to 6 carbon atoms. For example, the cycloalkyl group can be a cyclopropyl group, cyclobutyl group, cyclopentyl group or cyclohexyl group.

In the context of the present invention, the expression "cycloalkylalkyl group" especially means a group in which a linear, i.e., unbranched, or branched alkyl group, especially having 1 to 6 carbon atoms, is bonded to a cycloalkyl group, especially as defined or described in the preceding paragraph. The alkyl group can be a substituted or unsubstituted alkyl group. The cycloalkylalkyl group is preferably a cyclohexylmethyl group, a 1-cyclohexylethyl group or a 2-cyclohexylethyl group.

In the context of the present invention, the expression "alkyl group having 7 to 16 carbon atoms" means a linear, i.e., unbranched, or branched alkyl group having 7 to 16 carbon atoms. The alkyl group can be a substituted or unsubstituted alkyl group. The alkyl group having 7 to 16 carbon atoms is preferably an n-heptyl group, n-octyl group, tert-octyl group, n-nonyl group, n-decyl group, n-undecyl group, n-dodecyl group, n-tridecyl group, n-tetradecyl group, n-pentadecyl group or n-hexadecyl group.

In the context of the present invention, the expression "salt" used in connection with the dihydrotriazine compound of the general formula I can especially mean a salt with an organic acid, such as, for example, formic acid, acetic acid, propionic acid, lactic acid, butyric acid, isobutyric acid, malic acid, maleic acid, malonic acid, fumaric acid, succinic acid, succinic acid monoamide, glutaric acid, tartaric acid, oxalic acid, citric acid, glycolic acid, glucuronic acid, ascorbic acid, aspartic acid, glutamic acid, benzoic acid, phthalic acid, salicylic acid, anthranilic acid, benzenesulfonic acid, p-toluenesulfonic acid or methanesulfonic acid.

In the context of the present invention, the expression "antiseptic composition" is to be understood to mean a composition for reduction of microorganisms on animate surfaces, especially on mucosa and/or wounds, and/or for prevention, i.e., prophylaxis, or treatment of mucosa and/or wounds and/or for prevention and/or treatment of infections and/or infectious diseases.

The present invention is based, firstly, on the surprising finding that dihydrotriazine compounds of the general formula I or a tautomer thereof or a salt thereof have an improved efficacy against fungi, especially yeasts, compared to antiseptics of the type in question, such as, for example, polyhexamethylene biguanide or octenidine hydrochloride. As a result, what is possible in a particularly advantageous manner is better prevention or treatment of especially wounds and/or infections and/or infectious diseases that are caused or partly caused by fungi.

Furthermore, it has been found that, surprisingly, by combining a dihydrotriazine compound of the general formula I or a tautomer thereof or a salt thereof and a defoamer, it is possible to obtain a low-foam or foam-free composition, as a result of which, what is optimized or made possible in the first place is use of the dihydrotriazine compound especially for prevention or treatment of mucosa and/or wounds and/or infections and/or infectious diseases. Use of dihydrotriazine compounds of the general formula I or of tautomers thereof or of salts thereof for treatment and/or irrigation of mucosa and/or wounds was not to be expected because of the (in some cases) extreme foaming behavior thereof.

In one embodiment of the invention,
$R_1$ means a phenyl group or a phenylalkyl group, each of which is optionally substituted by 1 to 3 substituents selected from the group consisting of fluorine atom, chlorine atom, hydroxy group, methyl group, tert-butyl group, trifluoromethyl group and methoxy group,
$R_1'$ means a hydrogen atom which is bonded to the nitrogen atom at position 1 or 3 of the dihydrotriazine ring,
$R_2$ and $R_3$ both mean a methyl group and
$R_4$ means an n-octyl group, n-nonyl group or n-decyl group.

Preferably,
$R_1$ means a phenyl group, a benzyl group or a 2-phenylethyl group, each of which is optionally substituted by 1 to 3 substituents selected from the group consisting of fluorine atom, chlorine atom, hydroxy group, methyl group, tert-butyl group, trifluoromethyl group and methoxy group,
$R_1'$ means a hydrogen atom which is bonded to the nitrogen atom at position 1 or 3 of the dihydrotriazine ring,
$R_2$ and $R_3$ both mean a methyl group and
$R_4$ means an n-octyl group, n-nonyl group or n-decyl group.

Particularly preferably,
$R_1$ means a benzyl group which is optionally substituted by 1 to 3 substituents selected from the group consisting of fluorine atom, chlorine atom, hydroxy group, methyl group, tert-butyl group, trifluoromethyl group and methoxy group, preferably by 1 to 3 methyl groups, particularly preferably by one methyl group,
$R_1'$ means a hydrogen atom which is bonded to the nitrogen atom at position 1 or 3 of the dihydrotriazine ring,
$R_2$ and $R_3$ both mean a methyl group and
$R_4$ means an n-octyl group, n-nonyl group or n-decyl group.

In a further embodiment of the invention,
$R_1$ means a phenyl group, 4-chlorophenyl group, 2,4-difluorophenyl group, 2,3,4-trifluorophenyl group, 4-tert-butylphenyl group, 4-methoxyphenyl group, 2-methoxy-4-tert-butylphenyl group, 4-trifluoromethoxyphenyl group, benzyl group, methylbenzyl group such as, in particular, 4-methylbenzyl group, 4-methoxybenzyl group, 3,4-dimethoxybenzyl group, 4-hydroxybenzyl group, 3,4-dichlorobenzyl group, 2,3,4-trichlorobenzyl group, 4-trifluoromethylbenzyl group, 1-phenylethyl group, 2-phenylethyl group, 1-phenylpropyl group, 2-phenylpropyl group or 3-phenylpropyl group, preferably a methylbenzyl group, particularly preferably a 4-methylbenzyl group,
$R_1'$ means a hydrogen atom which is bonded to the nitrogen atom at position 1 or 3 of the dihydrotriazine ring,
$R_2$ and $R_3$ both mean a methyl group and
$R_4$ means an n-octyl group, n-nonyl group or n-decyl group.

In a further embodiment of the invention, $R_1$ means a methylbenzyl group, preferably 4-methylbenzyl group, and/or $R_2$ and $R_3$ both mean a methyl group and/or $R_4$ means an n-octyl group. Preferably, $R_1$ means a methylbenzyl group, preferably 4-methylbenzyl group, $R_2$ and $R_3$ both mean a methyl group and $R_4$ means an n-octyl group.

In a further embodiment of the invention, $R_1$ means a methylbenzyl group, preferably 4-methylbenzyl group, $R_1'$ means a hydrogen atom which is bonded to the nitrogen atom at position 1 or 3 of the dihydrotriazine ring, $R_2$ and $R_3$ both mean a methyl group and $R_4$ means an n-octyl group.

Particularly preferably, the dihydrotriazine compound has the formula Ia below:

Formula Ia

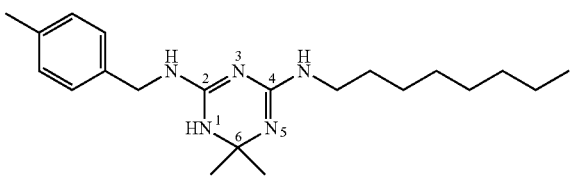

Alternatively, the dihydrotriazine compound can have the formula Ib below:

Formula Ib

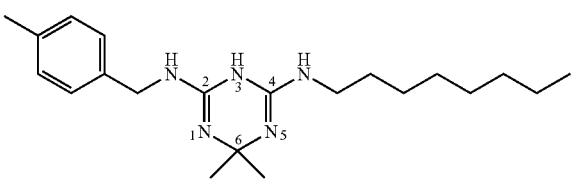

In a further embodiment of the invention, the dihydrotriazine compound or the salt thereof is 4-octylamino-1,6-dihydro-6,6-dimethyl-2-(4-methylbenzylamino)-1,3,5-triazine gluconate, which can also be referred to as 6,6-dimethyl-$N^2$-(4-methylbenzyl)-$N^4$-octyl-1,6-dihydro-[1,3,5]-triazine-2,4-diamine gluconate, or is a tautomer thereof. The dihydrotriazine compound or the salt thereof is preferably 4-octylamino-1,6-dihydro-6,6-dimethyl-2-(4'-methylbenzylamino)-1,3,5-triazine D-gluconate, which can also be referred to as 6,6-dimethyl-$N^2$-(4-methylbenzyl)-$N^4$-octyl-1,6-dihydro-[1,3,5]-triazine-2,4-diamine D-gluconate, or is a tautomer thereof. The dihydrotriazine compound disclosed in this paragraph or the dihydrotriazine compound salt disclosed in this paragraph has been found to be particularly effective for prevention or treatment of mucosa and/or wounds and/or infections and/or infectious diseases, especially of wounds and/or infections and/or infectious diseases that are caused or partly caused by fungi, especially yeasts.

The dihydrotriazine compound mentioned in the preceding paragraph or the dihydrotriazine compound salt 4-octylamino-1,6-dihydro-6,6-dimethyl-2-(4'-methylbenzylamino)-1,3,5-triazine D-gluconate mentioned in the preceding paragraph is commercially available under the designation "Femotaxidine" and can be represented by the formula Ia# below:

Formula Ia#

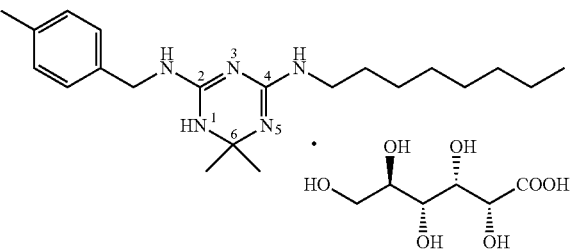

In a further embodiment of the invention, the dihydrotriazine compound of the general formula I or the salt thereof is 4-octylamino-3,6-dihydro-6,6-dimethyl-2-(4'-methylbenzylamino)-1,3,5-triazine gluconate, especially 4-octylamino-3,6-dihydro-6,6-dimethyl-2-(4'-methylbenzylamino)-1,3,5-triazine D-gluconate, or a tautomer thereof.

In a further embodiment of the invention, the dihydrotriazine compound of the general formula I or the tautomer thereof or the salt thereof has a proportion of 0.001% by weight to 1.00% by weight, especially 0.01% by weight to 0.50% by weight, preferably 0.025% by weight to 0.25% by weight, based on the total weight of the aqueous composition. Especially the proportions disclosed in this paragraph for the dihydrotriazine compound or the tautomer thereof or the salt thereof have been found to be particularly advantageous with respect to the prevention or treatment of mucosa and/or wounds and/or infections and/or infectious diseases, especially of wounds and/or infections and/or infectious diseases that are caused or partly caused by fungi, especially yeasts.

In a further embodiment of the invention, the defoamer is selected from the group consisting of alkyl amide, silicone, poloxamer and combinations, especially mixtures, of at least two of the defoamers mentioned.

The alkyl amide can be especially an alkyl amide of the formula $R_1$—NH—$R_2$, where $R_1$ is n-octyl, isooctyl or 2-ethylhexyl and $R_2$ is n-octane or isooctane, n-nonane or isononane or n-decane or isodecane. According to the invention, the alkyl amide can also be a combination, especially mixture, of at least two relevant alkyl amides.

The silicone can be a polydimethylsiloxane, polyether siloxane (siloxane polyethylene glycol or siloxane polypropylene glycol) or 3D-modified siloxane, also called crosslink siloxane, or a combination, especially mixture, of at least two of the silicones mentioned.

The poloxamer preferably has 2 to 130 —$CH_2$—$CH_2$—O— structural units and/or 15 to 67 —$CHCH_3$—$CH_2$—O— structural units per molecule.

In the context of the present invention, the expression "poloxamer" is to be understood to mean a block copolymer composed of ethylene oxide and propylene oxide.

In particular, the poloxamer can be poloxamer 407, poloxamer 188 or a combination, especially mixture, thereof.

Furthermore, the defoamer can be a combination, especially mixture, of an alkyl amide and a silicone. Such a combination of defoamers is particularly advantageous with respect to suppressing or weakening foaming of the dihydrazine compound or the tautomer thereof or the salt thereof. In this case, the alkyl amide can have a proportion, especially active proportion, of 0.0001% by weight to 0.1% by weight, especially 0.0005% by weight to 0.05% by weight, preferably 0.001% by weight to 0.05% by weight, based on the total weight of the aqueous composition, and the silicone can have a proportion, especially active proportion, of 0.00001% by weight to 0.01% by weight, especially 0.00002% by weight to 0.005% by weight, preferably 0.00005% by weight to 0.005% by weight, based on the total weight of the aqueous composition.

In a further embodiment of the invention, the defoamer has a proportion of 0.0001% by weight to 2.0% by weight, especially 0.0005% by weight to 1.5% by weight, preferably 0.001% by weight to 1.0% by weight, based on the total weight of the aqueous composition. Especially the defoamer proportions disclosed in this paragraph have been found to be particularly advantageous with respect to suppressing or weakening foaming due to the dihydrotriazine compound of the general formula I or the tautomer thereof or the salt thereof.

In a further embodiment of the invention, the aqueous composition further comprises a surfactant, especially a nonionic surfactant and/or a zwitterionic surfactant, with the proviso that the surfactant, especially the nonionic surfactant and/or the zwitterionic surfactant, and the defoamer are chosen such that they are different from one another, i.e., the surfactant and the defoamer are different compounds.

In the context of the present invention, the expression "nonionic surfactant" is intended to refer to a surfactant which does not contain any dissociable functional groups and therefore does not separate into ions in water or an aqueous liquid.

A nonionic or zwitterionic surfactant has especially the advantage that there is little or no interaction with the dihydrotriazine compound, and that, furthermore, it is very highly tolerated by mucosa and wounds.

The nonionic surfactant is preferably selected from the group consisting of poloxamer, fatty alcohol alkoxylate such as fatty alcohol ethoxylate, polyvinylpyrrolidone, alkyl polyglucoside and combinations, especially mixtures, of at least two of the nonionic surfactants mentioned. The nonionic surfactants which are mentioned in this paragraph and will be described in more detail below have been found to be particularly suitable for reducing or avoiding an irritation potential of the dihydrotriazine compound of the general formula I or the tautomer thereof or the salt thereof, which irritation potential is disadvantageous from the viewpoint of wound therapy.

The poloxamer preferably has 2 to 130 —$CH_2$—$CH_2$—O— structural units and/or 15 to 67 —$CHCH_3$—$CH_2$—O— structural units per molecule.

The poloxamer can be especially poloxamer 407, poloxamer 188 or a combination, especially mixture, thereof.

The use of a poloxamer as surfactant may be particularly preferred according to the invention, since poloxamers also have foam-dampening or foam-reducing properties and/or emulsifying properties in addition to surfactant properties. As a result, it is particularly advantageously possible to additionally dampen, diminish or suppress foaming due to the dihydrotriazine compound of the general formula I or the tautomer thereof or the salt thereof and/or to achieve or improve a homogeneous distribution of the defoamer within the aqueous composition.

The use of polyvinylpyrrolidone as surfactant may likewise be particularly preferred according to the invention, since this surfactant has emulsifying properties in addition to surfactant properties. The advantages further mentioned in the preceding paragraph apply mutatis mutandis. In addition, the use of polyvinylpyrrolidone has the advantage that it can bind water and thus act as a viscosity regulator.

In the context of the present invention, the expression "fatty alcohol alkoxylate" is to be understood to mean a nonionic surfactant, the lipophilic part of which comprises a fatty alcohol or consists of a fatty alcohol and the hydrophilic part of which comprises a polyalkylene glycol, especially a short-chain polyalkylene glycol, or consists of a polyalkylene glycol, especially a short-chain polyalkylene glycol. The fatty alcohol can be especially an alcohol derived from caprylic, capric, lauric, palmitic, stearic or oleic acid or branched isononyl, isoundecyl, isotridecyl, isopentadecyl or isononadecyl alcohols. In the context of the present invention, the fatty alcohol alkoxylate can also be referred to as polyalkylene glycol ether.

As already mentioned, the fatty alcohol alkoxylate can be especially a fatty alcohol ethoxylate.

The fatty alcohol ethoxylate is preferably a polyoxyethylene ether of lauryl alcohol, a polyoxyethylene ether of myristyl alcohol, a polyoxyethylene ether of cetyl alcohol, a polyoxyethylene ether of cetylstearyl alcohol, a polyoxyethylene ether of stearyl alcohol, a polyoxyethylene ether of oleyl alcohol, a polyoxyethylene ether of isononyl alcohol, a polyoxyethylene ether of isoundecyl alcohol, a polyoxyethylene ether of isotridecyl alcohol, a polyoxyethylene ether of isopentadecyl alcohol, a polyoxyethylene ether of isoheptadecyl alcohol, a polyoxyethylene ether of isononadecyl alcohol or a combination, especially mixture, of at least two of the polyoxyethylene ethers mentioned.

The fatty alcohol ethoxylate can especially be selected from the group consisting of polxoxyethylene (4) lauryl ether, polxoxyethylene (7) lauryl ether, polyoxyethylene (9) lauryl ether, polyoxyethylene (23) lauryl ether, polyoxyethylene (2) cetyl ether, polyoxyethylene (10) cetyl ether, polyoxyethylene (20) cetyl ether, polyoxyethylene (6) cetylstearyl ether, polyoxyethylene (20) cetylstearyl ether, polyoxyethylene (25) cetylstearyl ether, polyoxyethylene (2) stearyl ether, polyoxyethylene (10) stearyl ether, polyoxyethylene (20) stearyl ether, polyoxyethylene (2) oleyl ether, polyoxyethylene (10) oleyl ether, polyoxyethylene (20) oleyl ether, polyoxyethylene (10) monodecyl ether, polyoxyethylene (10) tridecyl ether and combinations, especially mixtures, of at least two of the fatty alcohol ethoxylates mentioned.

In other words, the fatty alcohol ethoxylate can especially be selected from the group consisting of laureth-4, laureth-7, laureth-9, laureth-23, ceteth-2, ceteth-10, ceteth-20, ceteareth-6, ceteareth-20, ceteareth-25, steareth-2, steareth-10, steareth-20, oleth-2, oleth-10, oleth-20, deceth-10, trideceth-10 and combinations, especially mixtures, of at least two of the fatty alcohol ethoxylates mentioned.

Fatty alcohol alkoxylates, especially fatty alcohol ethoxylates, have the advantage that they not only have surfactant properties, but also additionally have emulsifying action.

In the context of the present invention, the expression "alkyl polyglucoside" is to be understood to mean a nonionic sugar surfactant which comprises one or more glucose units and an alkyl radical, especially a long-chain alkyl radical, or consists of one or more glucose units and an alkyl radical, especially a long-chain alkyl radical. The glucose unit or glucose units acts/act as a hydrophilic component, whereas the alkyl radical represents the hydrophobic group.

The alkyl polyglucoside preferably comprises 1 to 5 glucose units and/or an alkyl radical having 6 carbon atoms to 20 carbon atoms, especially 6 carbon atoms to 16 carbon atoms, preferably 8 carbon atoms to 14 carbon atoms.

The alkyl polyglucoside is preferably a $C_8$- to $C_{20}$-alkyl polyglucose, especially $C_8$- to $C_{16}$-alkyl polyglucose.

The alkyl polyglucoside is particularly preferably lauryl polyglucose, decyl polyglucose, cocoyl polyglucose or a mixture of at least two of the alkyl polyglucosides mentioned. The alkyl radical of decyl polyglucose preferably has 8 carbon atoms to 16 carbon atoms, especially 10 carbon atoms. The alkyl radical of lauryl polyglucose preferably has 12 carbon atoms to 16 carbon atoms, especially 12 carbon atoms. The alkyl radical of cocoyl polyglucose preferably has 8 carbon atoms to 16 carbon atoms.

Alkyl polyglucosides, too, have the advantage that they not only have surfactant properties, but are also additionally emulsifying compounds.

In a further embodiment of the invention, the surfactant is a zwitterionic surfactant.

In the context of the present invention, the expression "zwitterionic surfactant" is intended to refer to a surfactant which has both a negatively and a positively charged functional group (so-called amphoteric surfactant).

The zwitterionic surfactant is preferably an alkylamidoalkyl betaine, especially an alkylamidoethyl betaine, alkylamidopropyl betaine or a combination, especially mixture, thereof.

The alkylamidoalkyl betaine is particularly preferably an alkylamidoalkyl betaine of a fatty acid. The fatty acid preferably has 8 to 18 carbon atoms. The fatty acid can be a saturated or unsaturated fatty acid. The fatty acid is preferably caprylic acid, capric acid, undecylenic acid (undec-10-enoic acid), undecylic acid (n-undecanoic acid), lauric acid, stearic acid, ricinoleic acid or coconut fatty acid.

The alkylamidoalkyl betaine is preferably selected from the group consisting of caprylamidoalkyl betaine, capramidoalkyl betaine, undecylenamidoalkyl betaine, undecylamidoalkyl betaine, lauramidoalkyl betaine, lauryldimethylaminoacetic acid betaine, stearamidoalkyl betaine, ricinoleamidoalkyl betaine, cocamidoalkyl betaine and combinations, especially mixtures, of at least two of the alkylamidoalkyl betaines mentioned.

The alkylamidoethyl betaine is preferably an alkylamidoethyl betaine based on a fatty acid, especially a fatty acid having 8 to 18 carbon atoms. The fatty acid can be a saturated or unsaturated fatty acid. The fatty acid is preferably caprylic acid, capric acid, undecylenic acid (undec-10-enoic acid), undecylic acid (n-undecanoic acid), lauric acid, stearic acid, ricinoleic acid or coconut fatty acid.

The alkylamidoethyl betaine is particularly preferably selected from the group consisting of caprylamidoethyl betaine, capramidoethyl betaine, undecylenamidoethyl betaine, undecylamidoethyl betaine, lauramidoethyl betaine, cocamidoethyl betaine, stearamidoethyl betaine, ricinoleamidoethyl betaine and combinations, especially mixtures, of at least two of the alkylamidoethyl betaines mentioned.

The alkylamidopropyl betaine is preferably an alkylamidopropyl betaine based on a fatty acid, especially a fatty acid having 8 to 18 carbon atoms. The fatty acid can be a saturated or unsaturated fatty acid. The fatty acid is preferably caprylic acid, capric acid, undecylenic acid (undec-10-enoic acid), undecylic acid (n-undecanoic acid), lauric acid, stearic acid, ricinoleic acid or coconut fatty acid.

The alkylamidopropyl betaine is particularly preferably selected from the group consisting of caprylamidopropyl betaine, capramidopropyl betaine, undecylenamidopropyl betaine, undecylamidopropyl betaine, cocamidopropyl betaine, stearamidopropyl betaine, ricinoleamidopropyl betaine and combinations, especially mixtures, of at least two of the alkylamidopropyl betaines mentioned.

The optionally provided surfactant can furthermore also be a combination, especially mixture, of the surfactants described in the preceding paragraphs, especially a combination, especially mixture, of a nonionic surfactant and a zwitterionic surfactant. In this respect, reference is made in full to the surfactants described in the preceding paragraphs.

Furthermore, the surfactant can be a poloxamer, wherein the aqueous composition does not comprise a defoaming compound and/or an emulsifying compound apart from the surfactant. The defoaming and/or emulsifying properties of a poloxamer, as already mentioned, mean that the additional use of a defoamer and/or emulsifier may be unnecessary in a particularly advantageous manner. With regard to further features and advantages of the poloxamer, reference is made in full to the prior description.

Furthermore, the surfactant can be polyvinylpyrrolidone, wherein the aqueous composition does not comprise a defoaming compound and/or an emulsifying compound and/or a water-binding compound apart from the surfactant. The defoaming and/or emulsifying and/or thickening, i.e., water-binding, properties of polyvinylpyrrolidone, as already mentioned, mean that the additional use of a defoamer and/or emulsifier and/or thickener may be unnecessary in a particularly advantageous manner. With regard to further features and advantages of polyvinylpyrrolidone, reference is made in full to the prior description.

Furthermore, the surfactant can be a fatty alcohol alkoxylate, especially fatty alcohol ethoxylate, and/or alkyl polyglucoside, wherein the aqueous composition does not comprise an emulsifying compound apart from the surfactant. The emulsifying properties of a fatty alcohol alkoxylate, especially fatty alcohol ethoxylate, and/or alkyl polyglucoside, as already mentioned, mean that the additional use of an emulsifier may be unnecessary in a particularly advantageous manner. With regard to further features and advantages of the fatty alcohol alkoxylate, especially fatty alcohol ethoxylate, and/or alkyl polyglucoside, reference is made in full to the prior description.

In a further embodiment of the invention, the surfactant has a proportion, especially active proportion, of 0.01% by weight to 10.0% by weight, especially 0.05% by weight to 2.0% by weight, preferably 0.1% by weight to 1.0% by weight, based on the total weight of the aqueous composition. Especially the surfactant proportions disclosed in this paragraph are particularly suitable for significantly reducing an irritating effect of the dihydrotriazine compound of the general formula I or the tautomer thereof or the salt thereof.

In a further embodiment of the invention, the aqueous composition further comprises an emulsifier, with the proviso that the emulsifier and an optionally present surfactant are chosen such that they are different from one another, i.e., the emulsifier and the surfactant are different compounds. The emulsifier is preferably selected from the group consisting of alcohol ethoxylate, alkyl polyglucoside, polysorbate, ethoxylated castor oil and combinations, especially mixtures, of at least two of the emulsifiers mentioned. With regard to further features and advantages of the surfactant, reference is made in full to the prior description.

The alcohol ethoxylate is preferably a fatty alcohol ethoxylate.

The fatty alcohol ethoxylate can be especially a polyoxyethylene ether of lauryl alcohol, a polyoxyethylene ether of myristyl alcohol, a polyoxyethylene ether of isononyl alcohol, a polyoxyethylene ether of isoundecyl alcohol, a polyoxyethylene ether of isotridecyl alcohol, a polyoxyethylene ether of cetyl alcohol, a polyoxyethylene ether of cetylstearyl alcohol, a polyoxyethylene ether of stearyl alcohol, a polyoxyethylene ether of oleyl alcohol or a combination, especially mixture, of at least two of the polyoxyethylene ethers mentioned.

The alcohol ethoxylate is preferably selected from the group consisting of polxoxyethylene (4) lauryl ether, polxoxyethylene (7) lauryl ether, polyoxyethylene (9) lauryl ether, polyoxyethylene (23) lauryl ether, polyoxyethylene (2) cetyl ether, polyoxyethylene (10) cetyl ether, polyoxyethylene (20) cetyl ether, polyoxyethylene (6) cetylstearyl ether, polyoxyethylene (20) cetylstearyl ether, polyoxyethylene (25) cetylstearyl ether, polyoxyethylene (2) stearyl ether, polyoxyethylene (10) stearyl ether, polyoxyethylene (20) stearyl ether, polyoxyethylene (2) oleyl ether, polyoxyethylene (10) oleyl ether, polyoxyethylene (20) oleyl ether, polyoxyethylene (10) monodecyl ether, polyoxyethylene (10) tridecyl ether and combinations, especially mixtures, of at least two of the fatty alcohol ethoxylates mentioned.

In other words, the alcohol ethoxylate can preferably be selected from the group consisting of laureth-4, laureth-7, laureth-9, laureth-23, ceteth-2, ceteth-10, ceteth-20, ceteareth-6, ceteareth-20, ceteareth-25, steareth-2, steareth-10, steareth-20, oleth-2, oleth-10, oleth-20, deceth-10, trideceth-10 and combinations, especially mixtures, of at least two of the fatty alcohol ethoxylates mentioned.

The alkyl polyglucoside preferably comprises 1 to 5 glucose units and/or an alkyl radical having 8 carbon atoms to 20 carbon atoms, especially 8 carbon atoms to 16 carbon atoms, preferably 8 carbon atoms to 14 carbon atoms.

The alkyl polyglucoside is preferably a $C_8$- to $C_{20}$-alkyl polyglucose, especially $C_8$- to $C_{16}$-alkyl polyglucose.

The alkyl polyglucoside is particularly preferably lauryl polyglucose, decyl polyglucose, cocoyl polyglucose or a mixture of at least two of the alkyl polyglucosides mentioned. The alkyl radical of decyl polyglucose preferably has 8 carbon atoms to 16 carbon atoms, especially 10 carbon atoms. The alkyl radical of lauryl polyglucose preferably has 12 carbon atoms to 16 carbon atoms, especially 12 carbon atoms. The alkyl radical of cocoyl polyglucose preferably has 8 carbon atoms to 16 carbon atoms.

In the context of the present invention, the expression "polysorbate" is to be understood to mean an ethoxylated sorbitan acid fatty acid ester.

The polysorbate can especially be selected from the group consisting of polyoxyethylene (20) sorbitan monolaurate, polyoxyethylene (4) sorbitan monolaurate, polyoxyethylene (20) sorbitan monopalmitate, polyoxyethylene (20) sorbitan monostearate, polyoxyethylene (4) sorbitan monostearate, polyoxyethylene (20) sorbitan tristearate, polyoxyethylene (20) sorbitan monooleate, polyoxyethylene (5) sorbitan monooleate, polyoxyethylene (20) sorbitan trioleate, polyoxyethylene (20) sorbitan monoisostearate and combinations, especially mixtures, of at least two of the polysorbates mentioned.

In other words, the polysorbate can especially be selected from the group consisting of polysorbate 20, polysorbate 21, polysorbate 40, polysorbate 60, polysorbate 61, polysorbate 65, polysorbate 80, polysorbate 81, polysorbate 85, polysorbate 120 and combinations, especially mixtures, of at least two of the polysorbates mentioned.

In a further embodiment of the invention, the emulsifier has a proportion of 0.001% by weight to 1.5% by weight, especially 0.01% by weight to 1.5% by weight, especially 0.02% by weight to 1.0% by weight, preferably 0.05% by weight to 0.5% by weight, based on the total weight of the aqueous composition. Especially the emulsifier proportions disclosed in this paragraph have been found to be particularly advantageous with respect to a homogeneous distribution of the defoamer within the aqueous composition.

In a further embodiment of the invention, the aqueous composition further comprises an additive selected from the group consisting of complexing agent, humectant, acid, alkali, organic solvent and combinations, especially mixtures, of at least two of the additives mentioned.

The complexing agent can especially be selected from the group consisting of citric acid, tartaric acid, succinic acid, methylglycine diacetate, ethyldiaminetetraacetate, N,N'-bis(carboxymethyl)-L-glutamate, polyaspartic acid, iminodisuccinate, salts of the complexing agents mentioned and combinations, especially mixtures, of at least two of the complexing agents mentioned.

Furthermore, the complexing agent can have a proportion of 0.01% by weight to 10.0% by weight, especially 0.02% by weight to 2.0% by weight, preferably 0.05% by weight to 1.0% by weight, based on the total weight of the aqueous composition.

The humectant can be selected from the group consisting of glycerol, polydextrose, sorbitol, ethylene glycol, polyethylene glycol, propylene glycol, butylene glycol, pentylene glycol, hexanediol, octanediol, glucose, fructose, glucuronic acid, lactose, lactic acid, lactate, lactulose, sucrose, hyaluronic acid, xylitol, xylose and combinations, especially mixtures, of at least two of the humectants mentioned.

Furthermore, the humectant can have a proportion of 0.05% by weight to 10.0% by weight, especially 0.1% by weight to 7.5% by weight, preferably 0.5% by weight to 5% by weight, based on the total weight of the aqueous composition.

The acid can be selected from the group consisting of formic acid, acetic acid, propionic acid, lactic acid, butyric acid, isobutyric acid, malic acid, maleic acid, malonic acid, fumaric acid, succinic acid, succinic acid monoamide, glutaric acid, tartaric acid, oxalic acid, citric acid, glycolic acid, glucuronic acid, ascorbic acid, aspartic acid, glutamic acid, benzoic acid, phthalic acid, salicylic acid, anthranilic acid, benzenesulfonic acid, p-toluenesulfonic acid, methanesulfonic acid and combinations, especially mixtures, of at least two of the acids mentioned.

Furthermore, the acid can have a proportion of 0.01% by weight to 10.0% by weight, especially 0.1% by weight to 6.0% by weight, preferably 0.1% by weight to 5.0% by weight, based on the total weight of the aqueous composition.

The alkalis can be selected from the group consisting of sodium hydroxide, potassium hydroxide, calcium hydroxide and magnesium hydroxide and combinations, especially mixtures, of at least two of the alkalis mentioned.

Furthermore, the alkalis can have a proportion of 0.01% by weight to 10.0% by weight, especially 0.1% by weight to 6.0% by weight, preferably 0.1% by weight to 5.0% by weight, based on the total weight of the aqueous composition.

The organic solvent can be selected from the group consisting of ethanol, propan-1-ol, propan-2-ol and combinations, especially mixtures, of at least two of the organic solvents mentioned.

Furthermore, the organic solvent can have a proportion of 0.1% by weight to 10.0% by weight, especially 0.5% by weight to 10.0% by weight, preferably 1.0% by weight to 10.0% by weight, based on the total weight of the aqueous composition.

The aqueous composition preferably has a proportion of water of >80% by weight, especially >90% by weight, based on the total weight of the aqueous composition.

In a further embodiment of the invention, the aqueous composition is an aqueous composition for application or use in the prevention or treatment of mucosa and/or wounds, especially acute or chronic wounds, and/or for application or use in the prevention or treatment of infections, especially infections caused or partly caused by fungi, especially yeasts, and/or for application or use in the prevention or treatment of infectious diseases, especially infectious diseases caused or partly caused by fungi, especially yeasts. The infectious diseases can be, for example, candidiasis or erysipelas.

DETAILED DESCRIPTION

Further features and advantages of the invention are revealed by the description of preferred exemplary embodiments that follows. Here, individual features can each be realized alone or in combination with one another. The exemplary embodiments that are described merely serve for further elucidation of the invention without restricting the invention thereto.

Example Section

1. Preparation of a Wound Irrigation Solution According to the Invention 9912.5 g of water were initially charged in a suitable mixing reactor. A stirrer was then adjusted such that a slight torus formed on the water surface. Thereafter, 25.00 g of Tween 20 (polysorbate 20) and 2.50 g of N-(2-ethylhexyl) isononanamide were added. 50.00 g of cocamidopropyl betaine (50%) were then added. 10.00 g of Femotaxidine were then added. Thereafter, the mixture was stirred for one hour. The solution obtained here had the composition reported in Table 1 below:

TABLE 1

| Example of a wound irrigation solution according to the invention | |
|---|---|
| Femotaxidine | 0.100% by weight |
| Purified water | 99.125% by weight |
| Cocamidopropyl betaine (50%) | 0.500% by weight |
| Tween 20 | 0.250% by weight |
| Alkyl amide | 0.025% by weight |

2. Preparation of a Further Wound Irrigation Solution According to the Invention 9889.0 g of water were initially charged in a suitable mixing reactor. A stirrer was then adjusted such that a slight torus formed on the water surface. Thereafter, 40.00 g of Tween 20 and 1.00 g of polyether siloxane were added. 50.00 g of cocamidopropyl betaine (50%) were then added. Lastly, 20.00 g of Femotaxidine were added. The mixture was stirred for one hour. The solution obtained here had the composition reported in Table 2 below:

TABLE 2

| Example of a wound irrigation solution according to the invention | |
|---|---|
| Femotaxidine | 0.200% by weight |
| Purified water | 98.890% by weight |
| Cocamidopropyl betaine (50%) | 0.500% by weight |
| Tween 20 | 0.400% by weight |
| Silicone | 0.010% by weight |

3. Preparation of a Further Wound Irrigation Solution According to the Invention 9885.0 g of water were initially charged in a suitable mixing reactor. A stirrer was then adjusted such that a slight torus formed on the water surface. Thereafter, 17.50 g of Laureth-7 and 2.50 g of N-(2-ethylhexyl)isononanamide were added. 90.00 g of undecylenamidopropyl betaine (35%) were then added. Lastly, 5.00 g of Femotaxidine were added. The mixture was stirred for one hour. The solution obtained here had the composition reported in Table 3 below:

TABLE 3

| Example of a further wound irrigation solution according to the invention | |
|---|---|
| Femotaxidine | 0.050% by weight |
| Purified water | 98.850% by weight |
| Undecylenamidopropyl betaine (35%) | 0.900% by weight |
| Laureth-7 | 0.175% by weight |
| Alkyl amide | 0.025% by weight |

4. Preparation of a Further Wound Irrigation Solution According to the Invention 9833.0 g of water were initially charged in a suitable mixing reactor. A stirrer was then adjusted such that a slight torus formed on the water surface. Thereafter, 15.00 g of Laureth-7 and 2.00 g of polyether siloxane were added. 125.0 g of undecylenamidopropyl betaine (35%) were then added. Lastly, 25.00 g of Femotaxidine were added. The mixture was stirred for one hour. The solution obtained here had the composition reported in Table 4 below:

TABLE 4

| Example of a further wound irrigation solution according to the invention | |
|---|---|
| Femotaxidine | 0.250% by weight |
| Purified water | 98.330% by weight |
| Undecylenamidopropyl betaine (35%) | 1.250% by weight |
| Laureth-7 | 0.150% by weight |
| Silicone | 0.020% by weight |

5. Preparation of a Further Wound Irrigation Solution According to the Invention 9904.4 g of water were initially charged in a suitable mixing reactor. A stirrer was then adjusted such that a slight torus formed on the water surface. Thereafter, 15.00 g of Laureth-7, 0.50 g of N-(2-ethylhexyl)isononanamide and 0.10 g of 3D-modified "crosslink" siloxanes were added. 70.00 g of caprylamidopropyl betaine (35%) were then added. Lastly, 10.00 g of Femotaxidine were added. The mixture was stirred for one hour. The solution obtained here had the composition reported in Table 5 below:

TABLE 5

| Example of a further wound irrigation solution according to the invention | |
|---|---|
| Femotaxidine | 0.100% by weight |
| Purified water | 99.044% by weight |
| Alkylamidopropyl betaine (35%) | 0.700% by weight |
| Laureth-7 | 0.150% by weight |
| Alkyl amide | 0.005% by weight |
| Silicone | 0.001% by weight |

6. Preparation of a Further Wound Irrigation Solution According to the Invention 9889.5 g of water were initially charged in a suitable mixing reactor. A stirrer was then adjusted such that a slight torus formed on the water surface. Thereafter, 20.00 g of Poloxamer 188 and 0.50 g of 3D-modified "crosslink" siloxanes were added. 50.00 g of cocamidopropyl betaine (50%) were then added. Lastly, 10.00 g of Femotaxidine were added. The mixture was stirred for one hour. The solution obtained here had the composition reported in Table 6 below:

TABLE 6

Example of a further wound irrigation solution according to the invention

| | |
|---|---|
| Femotaxidine | 0.100% by weight |
| Purified water | 98.895% by weight |
| Cocamidopropyl betaine (50%) | 0.800% by weight |
| Poloxamer | 0.200% by weight |
| Silicone | 0.005% by weight |

7. Preparation of a Further Wound Irrigation Solution According to the Invention 9958.0 g of water were initially charged in a suitable mixing reactor. A stirrer was then adjusted such that a slight torus formed on the water surface. Thereafter, 30.00 g of Tween 20 and 2.00 g of N-(2-ethylhexyl)isononanamide were added. 10.00 g of Femotaxidine were then added. Thereafter, the mixture was stirred for one hour. The solution obtained here had the composition reported in Table 7 below:

TABLE 7

Example of a further wound irrigation solution according to the invention

| | |
|---|---|
| Femotaxidine | 0.100% by weight |
| Purified water | 99.580% by weight |
| Tween 20 | 0.300% by weight |
| Alkyl amide | 0.020% by weight |

8. Preparation of a Further Wound Irrigation Solution According to the Invention 9966.4 g of water were initially charged in a suitable mixing reactor. A stirrer was then adjusted such that a slight torus formed on the water surface. Thereafter, 12.50 g of Laureth-7, 1.00 g of N-(2-ethylhexyl)isononanamide and 0.10 g of 3D-modified "crosslink" siloxanes were added. 20.00 g of Femotaxidine were then added. Thereafter, the mixture was stirred for one hour.

The solution obtained here had the composition reported in Table 8 below:

TABLE 8

Example of a further wound irrigation solution according to the invention

| | |
|---|---|
| Femotaxidine | 0.200% by weight |
| Purified water | 99.664% by weight |
| Laureth-7 | 0.125% by weight |
| Alkyl amide | 0.010% by weight |
| Silicone | 0.001% by weight |

9. Preparation of a Further Wound Irrigation Solution According to the Invention 9820.0 g of water were initially charged in a suitable mixing reactor. A stirrer was then adjusted such that a slight torus formed on the water surface. Thereafter, 500.00 g of polyvinylpyrrolidone were added. 70.00 g of undecylenamidopropyl betaine (35%) were then added. 10.00 g of Femotaxidine were then added. Thereafter, mixture was stirred for one hour. The solution obtained here had the composition reported in Table 9 below:

TABLE 9

Example of a further wound irrigation solution according to the invention

| | |
|---|---|
| Femotaxidine | 0.100% by weight |
| Purified water | 98.200% by weight |
| Polyvinylpyrrolidone | 5.000% by weight |
| Undecylenamidopropyl betaine (35%) | 0.700% by weight |

10. Preparation of a Further Wound Irrigation Solution According to the Invention 9890.0 g of water were initially charged in a suitable mixing reactor. A stirrer was then adjusted such that a slight torus formed on the water surface. Thereafter, 100.00 g of poloxamer 188 were added. 10.00 g of Femotaxidine were then added. Thereafter, the mixture was stirred for one hour. The solution obtained here had the composition reported in Table 10 below:

TABLE 10

Example of a further wound irrigation solution according to the invention

| | |
|---|---|
| Femotaxidine | 0.100% by weight |
| Purified water | 98.900% by weight |
| Poloxamer | 1.000% by weight |

11. Preparation of A Wound Irrigation Solution Not According to the Invention 9980.0 g of water were initially charged in a suitable mixing reactor. A stirrer was then adjusted such that a slight torus formed on the water surface. Thereafter, 20.00 g of Femotaxidine were added. Thereafter, the mixture was stirred for one hour. The solution obtained here had the composition reported in Table 11 below:

TABLE 11

Example of a wound irrigation solution not according to the invention

| | |
|---|---|
| Femotaxidine | 0.200% by weight |
| Purified water | 99.800% by weight |

The wound irrigation solutions according to the invention that were prepared in sections 1. to 10. exhibited great differences in foaming behavior compared to an aqueous Femotaxidine solution (0.1% by weight or 0.2% by weight [solution 11]). Whereas the foam in the case of the wound irrigation solutions according to the invention required much more energy for formation and then collapsed within a very short period of time, more particularly within a few minutes, the foam in the case of the aqueous Femotaxidine solution used for comparative purposes formed very readily and persisted over a period of over 10 hours. Formulations 5 and 8 in particular showed a very rapid breakdown of foam.

In comparison with the commercial preparation available under the registered trademark OCTENISEPT®, formulation 9, but also formulation 11, showed a distinctly more rapid efficacy against yeasts in accordance with EN13624 and could still also be convincing in the HET-CAM test with a distinctly lower irritation potential.

| EN 13624<br>Dirt conditions | C.<br>albicans 60 s | C.<br>albicans 90 s | C.<br>albicans 120 s | HET-<br>CAM |
|---|---|---|---|---|
| Formulation 9 | 4.5 | >4.5 | >4.5 | 1 |
| Formulation 11 | 4.5 | >4.5 | >4.5 | 2 |
| OCTENISEPT ® | — | — | 3.0 | 6 |

Reduction in microbial count in $\log_{10}$; criterion to pass the EN13624 test is >4.

The HET-CAM (hen's egg test on chorioallantoic membrane) is a method for testing the mucosal compatibility of chemicals. The CAM is the choroid of the egg. For the test, the substance to be tested is brought onto the CAM. The reactions of the membrane (bleedings, changes in the blood vessels or in the egg white) are observed, compared with a reference (e.g., sodium dodecyl sulfate) and evaluated. The test is acknowledged as the official preliminary test for testing mucosal compatibility.

In the HET-CAM, a 6 means a moderate irritation, whereas values of 1-5 are rated as low irritation.

The invention claimed is:

1. An aqueous composition comprising:
   a dihydrotriazine compound of the general formula I below:

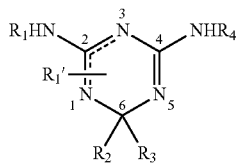

Formula I wherein
$R_1$ is (i) a phenyl group or a phenylalkyl group which is substituted with 1 to 3 substituents selected from the group consisting of $C_{1-6}$-alkoxy group, hydroxy group, a halogen atom, $C_{1-6}$-haloalkyl group, $C_{1-6}$-alkyl group, a sulfonamido group and $C_{1-6}$-haloalkoxy group, (ii) a naphthyl group or a naphthylalkyl group, (iii) a heterocyclic group, a heterocyclic alkyl group or a heterocyclic aminoalkyl group, (iv) an alkyl group having 1 to 16 carbon atoms or (v) a cycloalkyl group or a cycloalkylalkyl group,
$R'$ is a hydrogen atom which is bonded to the nitrogen atom at position 1 or 3 of the dihydrotriazine ring,
$R_2$ and $R_3$ independently of one another mean is a hydrogen atom or a methyl group,
$R_4$ is an alkyl group having 7 to 16 carbon atoms and the dashed line indicates that the position of a double bond is either between positions 1 and 2 or between positions 2 and 3 of the dihydrotriazine ring,
or a tautomer thereof or a salt thereof and
a defoamer.

2. The aqueous composition as claimed in claim 1, wherein $R_1$ is a phenyl group or a phenylalkyl group which is substituted by 1 to 3 substituents selected from the group consisting of fluorine atom, chlorine atom, hydroxy group, methyl group, tert-butyl group, trifluoromethyl group and methoxy group, $R_1'$ is a hydrogen atom which is bonded to the nitrogen atom at position 1 or 3 of the dihydrotriazine ring, $R_2$ and $R_3$ both mean a methyl group and $R_4$ is an n-octyl group, n-nonyl group or n-decyl group.

3. The aqueous composition as claimed in claim 2, wherein the phenylalkyl group is benzyl group.

4. The aqueous composition as claimed in claim 1, wherein $R_1$ is a phenyl group, 4-chlorophenyl group, 2,4-difluorophenyl group, 2,3,4-trifluorophenyl group, 4-tert-butylphenyl group, 4-methoxyphenyl group, 2-methoxy-4-tert-butylphenyl group, 4-trifluoromethoxyphenyl group, benzyl group, methylbenzyl group, 4-methylbenzyl group, 4-methoxybenzyl group, 3,4-dimethoxybenzyl group, 4-hydroxybenzyl group, 3,4-dichlorobenzyl group, 2,3,4-trichlorobenzyl group, 4-trifluoromethylbenzyl group, 1-phenylethyl group, 2-phenylethyl group, 1-phenylpropyl group, 2-phenylpropyl group or 3-phenylpropyl group, $R_1'$ means is a hydrogen atom which is bonded to the nitrogen atom at position 1 or 3 of the dihydrotriazine ring, $R_2$ and $R_3$ both mean a methyl group and $R_4$ is an n-octyl group, n-nonyl group or n-decyl group.

5. The aqueous composition as claimed in claim 1, wherein $R_1$ is a methylbenzyl group, and/or $R_2$ and $R_3$ both mean a methyl group and/or $R_4$ is an n-octyl group.

6. The aqueous composition as claimed in claim 5, wherein the methylbenzyl group is 4-methylbenzyl group.

7. The aqueous composition as claimed in claim 1, wherein $R_1$ means is a methylbenzyl group, $R_1'$ is a hydrogen atom which is bonded to the nitrogen atom at position 1 or 3 of the dihydrotriazine ring, $R_2$ and $R_3$ both mean a methyl group and $R_4$ is an n-octyl group.

8. The aqueous composition as claimed in claim 7, wherein the methylbenzyl group is 4-methylbenzyl group.

9. The aqueous composition as claimed in claim 1, wherein the dihydrotriazine compound is 4-octylamino-1,6-dihydro-6,6-dimethyl-2-(4'-methylbenzylamino)-1,3,5-triazine gluconate, 4-octylamino-3,6-dihydro-6,6-dimethyl-2-(4'-methylbenzylamino)-1,3,5-triazine gluconate, or a tautomer thereof.

10. The aqueous composition as claimed in claim 1, wherein the dihydrotriazine compound has a proportion of 0.001% by weight to 1.00% by weight based on the total weight of the aqueous composition.

11. The aqueous composition as claimed in claim 1, wherein the defoamer is selected from the group consisting of alkyl amide, silicone, poloxamer and combinations of at least two of the defoamers mentioned.

12. The aqueous composition as claimed in claim 1, wherein the defoamer has a proportion of 0.0001% by weight to 2.0% by weight based on the total weight of the aqueous composition.

13. The aqueous composition as claimed in claim 1, wherein the aqueous composition further comprises a surfactant, the defoamer and the surfactant being different from one another.

14. The aqueous composition as claimed in claim 13, wherein the surfactant has an active proportion of 0.01% by weight to 10.0% by weight based on the total weight of the aqueous composition, and/or the emulsifier has a proportion of 0.001% by weight to 1.5% by weight based on the total weight of the aqueous composition.

15. The aqueous composition as claimed in claim 13, wherein the surfactant is a nonionic surfactant.

16. The aqueous composition as claimed in claim 13, wherein the surfactant is selected from the group consisting of poloxamer, fatty alcohol alkoxylate, polyvinylpyrrolidone, alkyl polyglucoside and combinations of at least two of the surfactants mentioned.

17. The aqueous composition as claimed in claim 1, wherein the surfactant is a zwitterionic surfactant.

18. The aqueous composition as claimed in claim 17, wherein the zwitterionic surfactant is an alkylamidoalkyl betaine.

19. The aqueous composition as claimed in claim 18, wherein the alkylamidoalkyl betaine is an alkylamidoethyl betaine, alkylamidopropyl betaine or a combination thereof.

20. The aqueous composition as claimed in claim 1, wherein the aqueous composition further comprises an emulsifier and a surfactant, the emulsifier and the surfactant being different from one another.

21. The aqueous composition as claimed in claim 20, wherein the emulsifier is selected from the group consisting of alcohol ethoxylate, alkyl polyglucoside, polysorbate, ethoxylated castor oil and combinations of at least two of the emulsifiers mentioned.

22. The aqueous composition as claimed in claim 1, wherein the aqueous composition further comprises an additive selected from the group consisting of thickener, complexing agent, humectant, acid, alkali, organic solvent and combinations of at least two of the additives mentioned.

23. The aqueous composition as claimed in claim 1, wherein the aqueous composition is in the form of an aqueous solution or a hydrogel.

24. A method for preventing or treating mucosa and/or wounds and/or infections and/or infectious diseases comprising the step of administering an aqueous composition as claimed in claim 1 to a patient.

\* \* \* \* \*